United States Patent
Zhu et al.

(10) Patent No.: US 10,481,096 B2
(45) Date of Patent: *Nov. 19, 2019

(54) METHOD OF DETECTING SINGLE MOLECULES

(71) Applicants: Tsinghua University, Beijing (CN); HON HAI PRECISION INDUSTRY CO., LTD., New Taipei (TW)

(72) Inventors: Zhen-Dong Zhu, Beijing (CN); Qun-Qing Li, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/990,933

(22) Filed: May 29, 2018

(65) Prior Publication Data

US 2018/0348139 A1 Dec. 6, 2018

(30) Foreign Application Priority Data

Jun. 6, 2017 (CN) .......................... 2017 1 0416318

(51) Int. Cl.
*G01N 21/65* (2006.01)
*B82Y 15/00* (2011.01)

(52) U.S. Cl.
CPC ............ *G01N 21/658* (2013.01); *B82Y 15/00* (2013.01); *G01N 2021/651* (2013.01)

(58) Field of Classification Search
CPC . G01N 21/658; G01N 2021/651; B82Y 15/00
See application file for complete search history.

(56) References Cited

U.S. PATENT DOCUMENTS 10,215,896 B2 * 2/2019 Zhu .......................... C23F 1/02
2012/0081703 A1 * 4/2012 Moskovits ........... G01N 21/658
356/301

(Continued)

FOREIGN PATENT DOCUMENTS

CN 103868909 A 6/2014

OTHER PUBLICATIONS

Wanbo Li, Xueqin Jiang, Jiancai Xue, Zhangkai Zhou, Jianhua Zhou, "Antibody modified gold nano-mushroom arrays for rapid detection of alpha-fetoprotein" Biosensors and Bioelectronics, vol. 68, pp. 468-474, Jun. 15, 2014, http://doi.org/10.1016/j.bios.2015.01.033.

*Primary Examiner* — Dominic J Bologna
(74) *Attorney, Agent, or Firm* — ScienBiziP, P.C.

(57) ABSTRACT

A method of detecting single molecule includes: providing a carrier, wherein the carrier includes a substrate, and a plurality of three-dimensional nanostructures are located on the substrate; disposing single molecule samples on the plurality of three-dimensional nanostructures; detecting the single molecule samples with a detector; wherein each three-dimensional nanostructure includes a first rectangular structure, a second rectangular structure, and a triangular prism structure; the first rectangular structure, the second rectangular structure, and the triangular prism structure are stacked in that order, a first width of a bottom surface of the triangular prism structure is equal to a second width of a first top surface of the second rectangular structure and greater than a third width of a second top surface of the first rectangular structure, and the first rectangular structure comprises a first metal and the triangular prism structure comprises a second metal.

14 Claims, 13 Drawing Sheets

(56) References Cited

U.S. PATENT DOCUMENTS

| | | | | |
|---|---|---|---|---|
| 2012/0113419 A1* | 5/2012 | Wang | ................. | B82Y 15/00 356/301 |
| 2012/0182550 A1* | 7/2012 | Tang | ................. | G01N 21/658 356/301 |
| 2012/0188539 A1* | 7/2012 | Stuke | ................. | B82Y 20/00 356/301 |
| 2013/0115413 A1* | 5/2013 | Eres | ................. | G01N 21/01 428/120 |
| 2015/0233833 A1* | 8/2015 | Shibayama | ......... | G01N 21/658 356/244 |
| 2016/0169886 A1* | 6/2016 | Chou | ............ | G01N 33/54393 506/9 |
| 2018/0313987 A1* | 11/2018 | Zhu | ................. | G02B 5/1809 |

\* cited by examiner

METHOD OF DETECTING SINGLE MOLECULES

CROSS-REFRERENCE TO RELATED APPLICATIONS

This application is related to co-pending applications entitled, "SOLAR CELL", U.S. patent application Ser. No. 15/990,929, concurrently filed on May 29, 2018 ,"LIGHT EMITTING DIODE", U.S. patent application Ser. No. 15/990,958, concurrently filed on May 29, 2018.

FIELD

The subject matter herein generally relates to a method of detecting single molecules.

BACKGROUND

Raman spectroscopy is widely used for single molecule detection.

A method for detecting single molecules using Raman spectroscopy is provided. An aggregated silver particle film is coated on a surface of a glass substrate. A number of single molecule samples are disposed on the aggregated silver particle film. A laser irradiation is supplied to the single molecule samples by a Raman detection system to cause a Raman scattering and produce a Raman spectroscopy. The Raman spectroscopy is received by a sensor and analyzed by a computer. However, the surface of the glass substrate is usually smooth. Thus, the Raman scattering signal is not strong enough and the resolution of the single molecule is relatively low. Therefore, the glass substrate coated with aggregated silver particle film is not suitable for detecting low concentration single molecule samples.

Thus, there is room for improvement within the art.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views. Implementations of the present technology will now be described, by way of example only, with reference to the attached figures, wherein.

DETAILED DESCRIPTION

Figure 1:
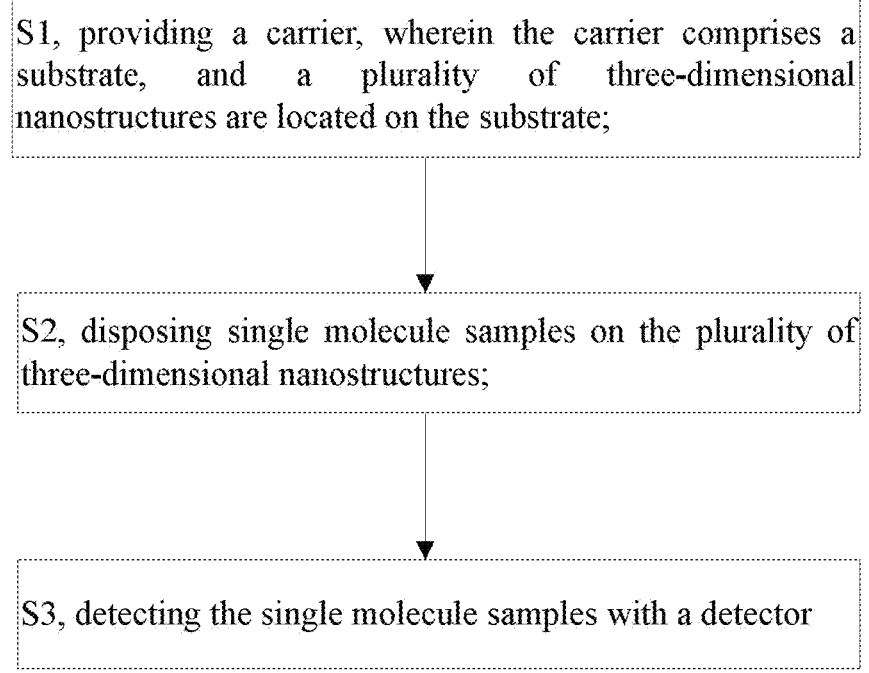
FIG. 1 is a flow chart of one embodiment of a method of detecting single molecules.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated to better illustrate details and features. The description is not to be considered as limiting the scope of the embodiments described herein.

Several definitions that apply throughout this invention will now be presented.

The connection can be such that the objects are permanently connected or releasably connected. The term "substantially" is defined to be essentially conforming to the particular dimension, shape or other word that substantially modifies, such that the component need not be exact. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

Referring to FIG. 1, an embodiment of a method of detecting single molecules includes following steps:

S1, providing a carrier 10, wherein the carrier 10 includes a substrate 100, and a plurality of three-dimensional nanostructures 110 are located on the substrate 100;

S2, disposing single molecule samples on the plurality of three-dimensional nanostructures 110;

S3, detecting the single molecule samples with a detector.

Figure 2:
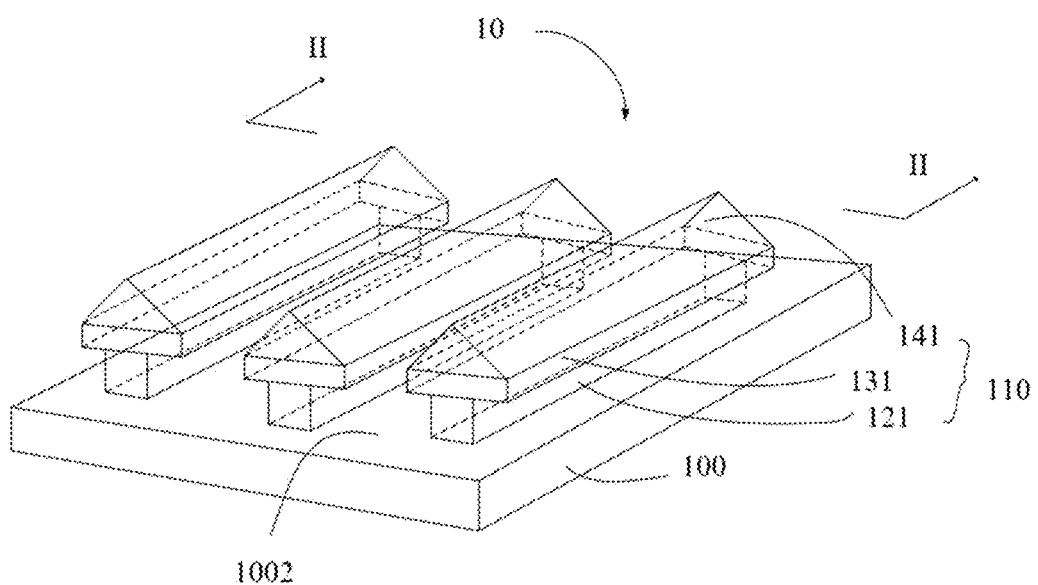
FIG. 2 is a structural schematic view of one embodiment of a carrier for single molecule detection.
Figure 3:
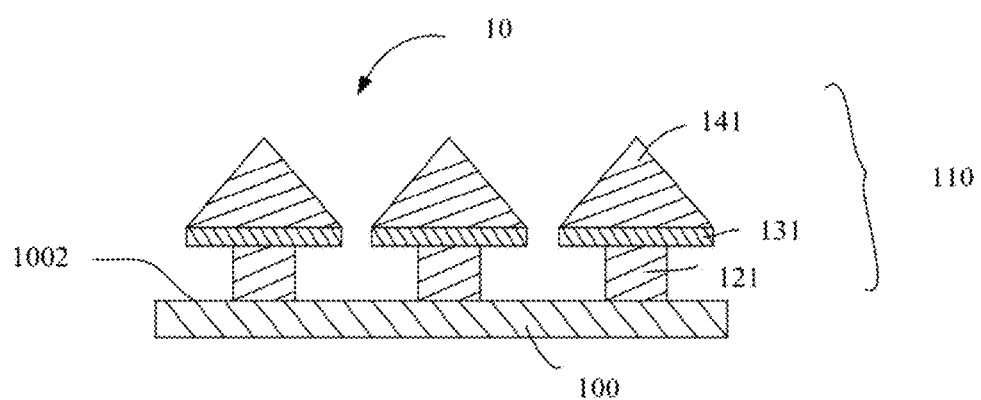
FIG. 3 is a sectional view of the carrier for single molecule detection of FIG. 2.

In step S1, referring to FIG. 2 and FIG. 3, the carrier 10 includes the substrate 100 and the plurality of three-dimensional nanostructures 110 located on at least one surface of the substrate 100. The three-dimensional nanostructure 110 is a pine shaped structure.

The substrate 100 can be an insulative substrate or a semiconductor substrate. The substrate 100 can be made of a material such as glass, quartz, silicon (Si), silicon dioxide ($SiO_2$), silicon nitride ($Si_3N_4$), gallium nitride (GaN), gallium arsenide (GaAs), sapphire, alumina, or magnesia (MgO). The size and thickness of the substrate 100 can be selected according to need. In one embodiment, the material of the substrate 100 is quartz.

Figure 4:
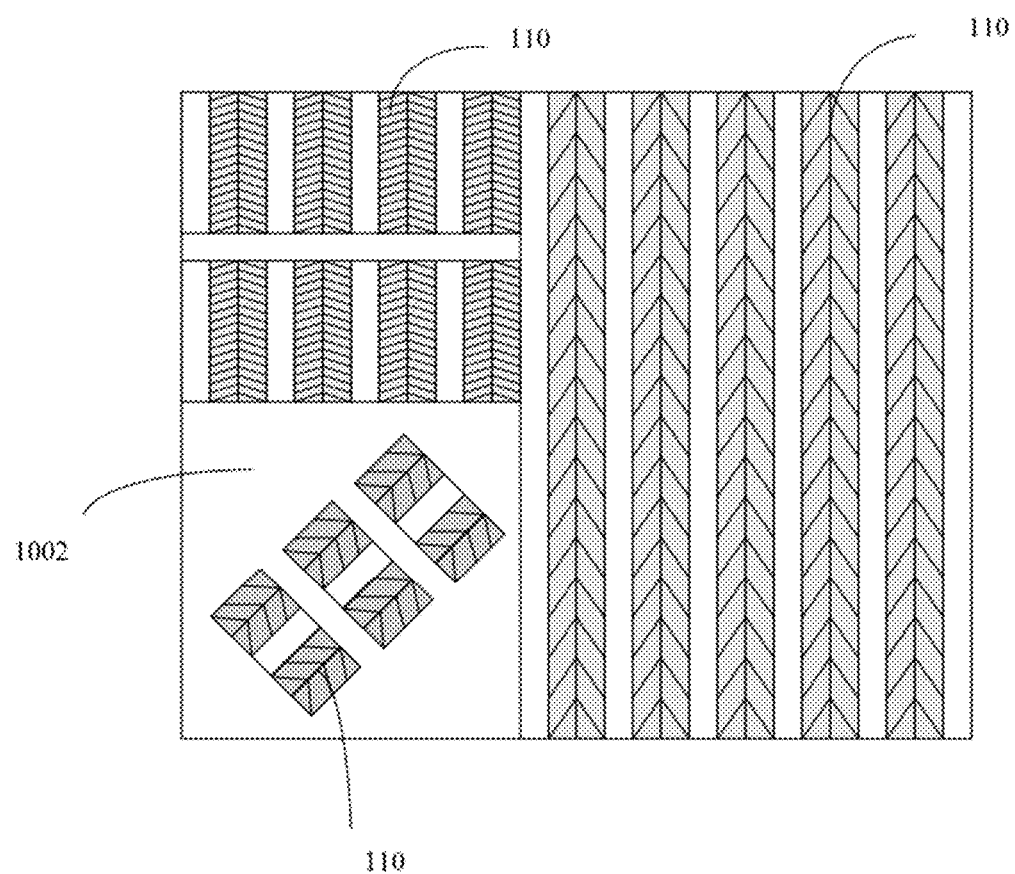
FIG. 4 is a structural schematic view of the carrier with a plurality of patterns.

The plurality of three-dimensional nanostructures 110 can be arranged side by side and extend along a straight line, a fold line, or a curve line. The extending direction is parallel to a first surface 1002 of the substrate 100. Referring to FIG. 4, the extending direction can be any direction which is parallel to the first surface 1002 of the substrate 100. The term "side by side" means that two adjacent three-dimensional nanostructures 110 are substantially parallel with each other along the extending direction. The distance between two adjacent three-dimensional nanostructures 110 is in a range from 0 nanometer to 200 nanometers. The plurality of three-dimensional nanostructures 110 can be continuous or discontinuous along the extending direction. In one exemplary embodiment, the plurality of three-dimensional nanostructures 110 are continuous, the extending direction of the three-dimensional nanostructures 110 extends side by side, the three-dimensional nanostructures are strip-shaped structures, and cross sections of the three-dimensional nanostructures have the same pine shapes and the same area.

The three-dimensional nanostructures 110 are pine shaped ridges located on the first surface 1002 of the substrate 100. The pine shaped ridges comprise a first rectangular structure 121, a second rectangular structure 131, and a triangular prism structure 141. The first rectangular structure 121 comprises a first top surface 1212, and the first top surface 1212 is away from the substrate 100. The second rectangular structure 131 is located on the first top surface 1212. The second rectangular structure 131 comprises a second top surface 1312, and the second top surface 1312 is away from the first rectangular structure 121. The triangular prism structure 141 is located on the second top surface 1312. The geometric centers of the first rectangular structure 121, the second rectangular structure 131 and the triangular prism structure 141 are on the same axis. The first rectangular structure 121 and the triangular prism structure 141 are both metal layers. The second rectangular structure 131 can isolate the first rectangular structure 121 and the triangular prism structure 141.

Figure 5:
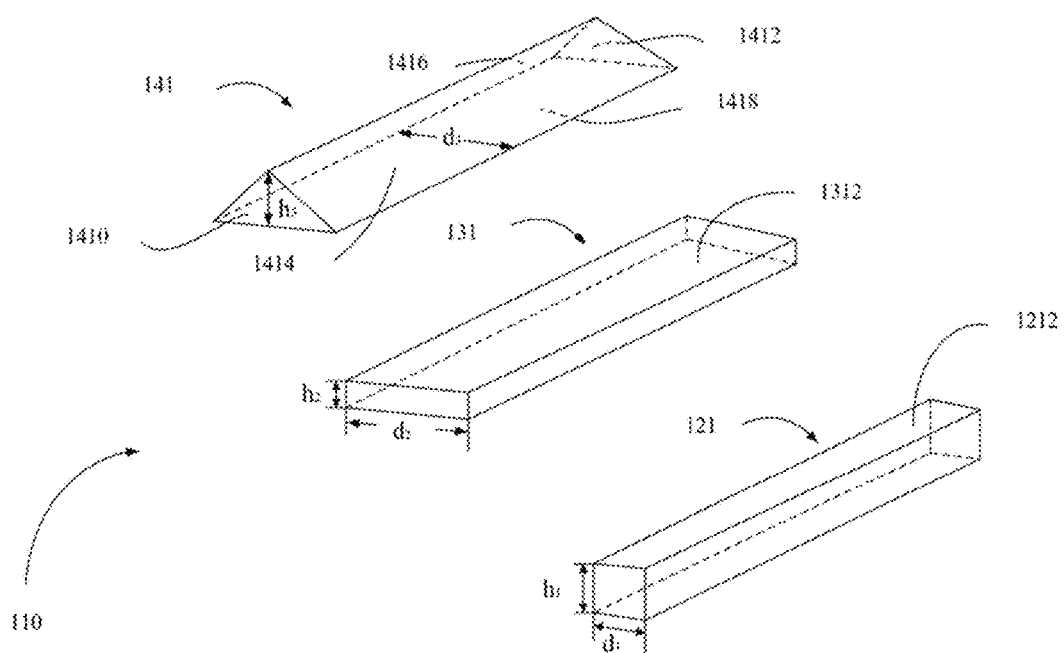
FIG. 5 is an exploded view of one embodiment of the three-dimensional nanostructures.

Referring to FIG. 5, the triangular prism structure 141 comprises a first triangle surface 1410 and a second triangle surface 1412 opposite to and substantially parallel with the first triangle surface 1410. The sizes and shapes of the first triangle surface 1410 and the second triangle surface 1412 are both the same. The triangular prism structure 141 further comprises a first rectangular side 1414, a second rectangular side 1416, and a third rectangular side 1418 connected to the first triangle surface 1410 and the second triangle surface 1412. The projection of the first triangle surface 1410 coincides with the projection of the second triangle surface 1412. The shapes of the first triangle surface 1410 and the second triangle surface 1412 are both isosceles triangle. The third rectangular side 1418 is in contact with the second top surface 1312 of the second rectangular structure 131. The side surface of the first rectangular structure 121 is perpendicular to the first surface 1002 of the substrate 100. The side surface of the second rectangular structure 131 is perpendicular to the first top surface 1212 of the first rectangular structure 121, thus the side surface of the second rectangular structure 131 is also perpendicular to the first surface 1002 of the substrate 100.

The width $d_1$ of the first rectangular structure 121 is in a range of 5 nanometers to 400 nanometers, the height $h_1$ of the first rectangular structure 121 is in a range of 20 nanometers to 500 nanometers. Furthermore, the width $d_1$ of the first rectangular structure 121 can be in a range of 12 nanometers to 320 nanometers, the height $h_1$ of the first rectangular structure 121 can be in a range of 50 nanometers to 200 nanometers. In one exemplary embodiment, the width $d_1$ of the first rectangular structure 121 is 50 nanometers, the height $h_1$ of the first rectangular structure 121 is 100 nanometers. The width $d_2$ of the second rectangular structure 131 is in a range of 50 nanometers to 450 nanometers, the height $h_2$ of the second rectangular structure 131 is in a range of 5 nanometers to 100 nanometers. Furthermore, the width $d_2$ of the second rectangular structure 131 can be in a range of 80 nanometers to 380 nanometers, the height $h_2$ of the second rectangular structure 131 can be in a range of 5 nanometers to 60 nanometers. In one exemplary embodiment, the width $d_2$ of the second rectangular structure 131 is 100 nanometers, the height $h_2$ of the second rectangular structure 131 is 10 nanometers. The width $d_3$ of the triangular prism structure 141 is in a range of 50 nanometers to 450 nanometers, the height $h_3$ of the triangular prism structure 141 is in a range of 40 nanometers to 800 nanometers. Furthermore, the width $d_3$ of the triangular prism structure 141 can be in a range of 80 nanometers to 380 nanometers, the height $h_3$ of the triangular prism structure 141 can be in a range of 130 nanometers to 400 nanometers. In one exemplary embodiment, the width $d_3$ of the triangular prism structure 141 is 100 nanometers, the height $h_3$ of the triangular prism structure 141 is 200 nanometers. The width $d_3$ of the triangular prism structure 141 is the width of the third rectangular side 1418 of the triangular prism structure 141. The width $d_3$ of the triangular prism structure 141 is equal to the width $d_2$ of the second rectangular structure 131. The third rectangular side 1418 of the triangular prism structure 141 is completely coincident with the second top surface 1312 of the second rectangular structure 131. The width $d_3$ of the triangular prism structure 141 is greater than the width $d_1$ of the first rectangular structure 121.

Figure 6:
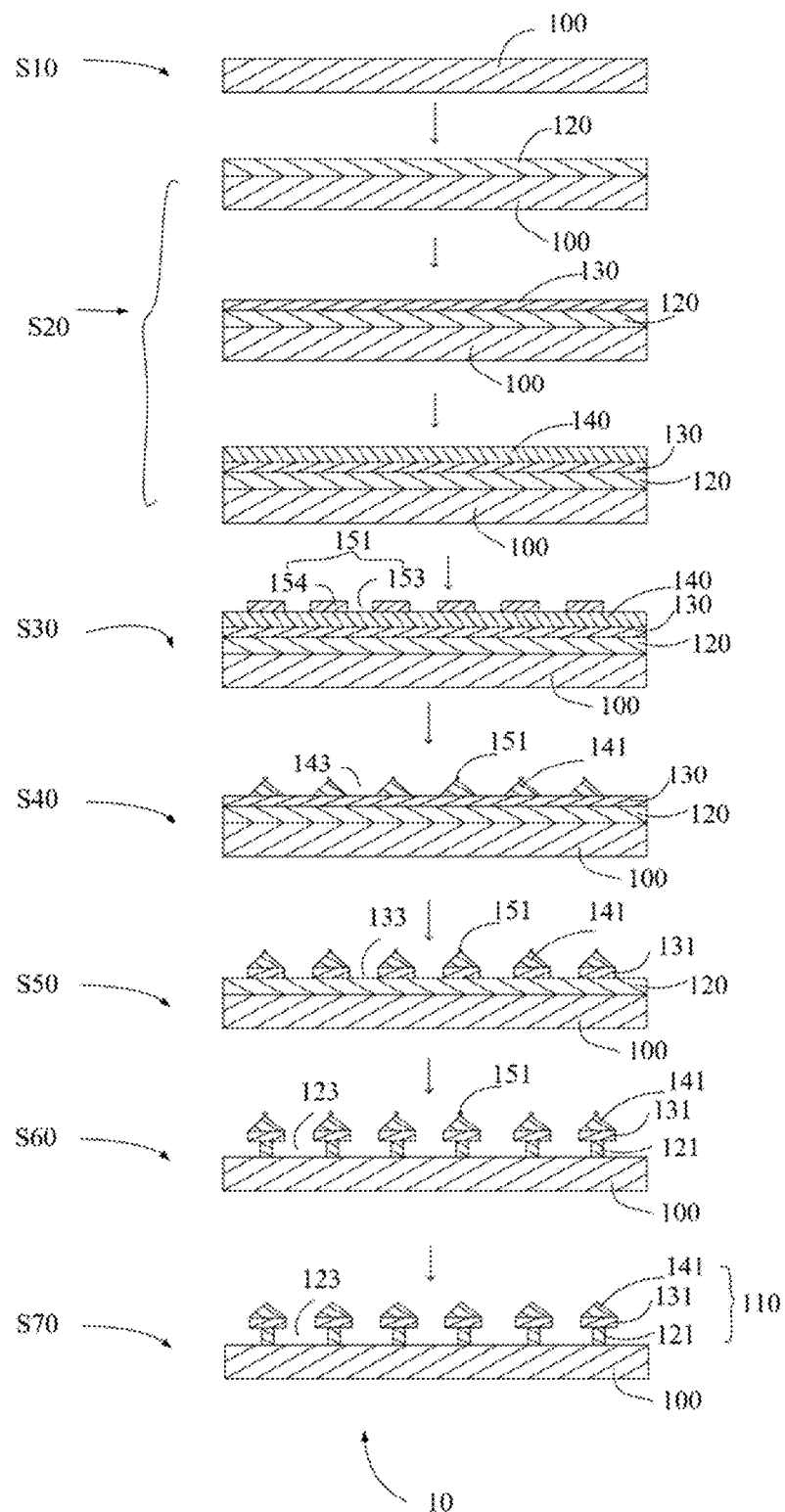
FIG. 6 is a flow chart of one embodiment of a method for making the carrier.

Referring to FIG. 6, an embodiment of a method of making the carrier 10 comprises:

S10, providing a substrate 100;

S20, forming a first metal layer 120 on the substrate 100, forming an isolation layer 130 on the first metal layer 120, and locating a second metal layer 140 on the isolation layer 130;

S30, placing a first mask layer 151 on the second metal layer 140, wherein the first mask layer 151 covers partial surface of the second metal layer 140, and other surface is exposed;

S40, etching the first mask layer 151 and the second metal layer 140 using the first mask layer 151 as a mask to obtain a plurality of parallel and spaced triangular prism structures 141;

S50, etching the isolation layer 130 using the plurality of triangular prism structures 141 as a mask to obtain a plurality of parallel and spaced second rectangular structures 131;

S60, etching the first metal layer 120 using the plurality of second rectangular structures 131 as a mask to obtain a plurality of parallel and spaced first rectangular structures 121; and S70, removing the first mask layer 151 to obtain the carrier 10.

In step S10, the substrate 100 can be an insulating substrate or a semiconductor substrate which includes a smooth surface. The material of the substrate 100 can be glass, quartz, gallium nitride, gallium arsenide, sapphire, alumina, magnesium oxide, silicon, silicon dioxide, or silicon nitride. The size, thickness and shape of the substrate 100 can be selected according to need. In one exemplary embodiment, the material of the substrate 100 is quartz. The substrate 100 can be cleaned by using a standard process. Furthermore, the substrate 100 can be treated with a hydrophilic treatment.

In step S20, the first metal layer 120 is deposited on the substrate 100, and the second metal layer 140 is deposited on the isolation layer 130. The method of depositing the first metal layer 120 and the second metal layer 140 can be electron beam evaporation method or ion sputtering method. The material of the first metal layer 120 and the second metal layer 140 can be metals with surface plasmon polaritons, such as gold, silver, copper, and aluminum. In one exemplary embodiment, the material of the first metal layer 120 and the second metal layer 140 is gold. The thickness of the first metal layer 120 is in a range of 20 nanometers to 500 nanometers. Furthermore, the thickness of the first metal layer 120 can be in a range of 50 nanometers to 200 nanometers. In one exemplary embodiment, the thickness of the first metal layer 120 is 100 nanometers. The thickness of the second metal layer 140 should be greater than 40 nanometers so that the second metal layer 140 can be a free-standing structure after removing the first mask layer 151. The free-standing structure is that the second metal layer 140 can keep a certain shape without any supporter. The thickness of the second metal layer 140 can be in a range of 40 nanometers to 800 nanometers. Furthermore, the thickness of the second metal layer 140 can be in a range of 130 nanometers to 400 nanometers. In one exemplary embodiment, the thickness of the second metal layer 140 is 200 nanometers.

The isolation layer 130 is used to isolate the first metal layer 120 and the second metal layer 140, thus the first metal layer 120 is not destroyed when the second metal layer 140 is etched. When the material of the first metal layer 120 is different from the material of the second metal layer 140, the isolation layer 130 can be omitted. The material of the isolation layer 130 can be metal or metal oxide, such as chromium, tantalum, tantalum oxide, titanium dioxide, silicon, or silicon dioxide. The thickness of the isolation layer 130 can be in a range of 5 nanometers to 100 nanometers. Furthermore, the thickness of the isolation layer 130 can be in a range of 5 nanometers to 60 nanometers. When the material of the isolation layer 130 is metal, the material of the isolation layer 130 should be different from the material of the first metal layer 120 and the second metal layer 140. In one exemplary embodiment, the material of the isolation layer 130 is chromium, and the thickness of the isolation layer 130 is 10 nanometers.

In step S30, the method for making the first mask layer 151 can be optical etching method, plasma etching method, electron beam etching method, focused ion beam etching method, hot embossing method, or nanoimprinting method. In one exemplary embodiment, the first mask layer 151 is formed on the second metal layer 140 by nanoimprinting method. Compared with other methods, the nanoimprinting method for making the first mask layer 151 has a plurality of advantages, such as high precision, high efficiency, low energy consumption, low temperature operation, and low cost.

Figure 7:
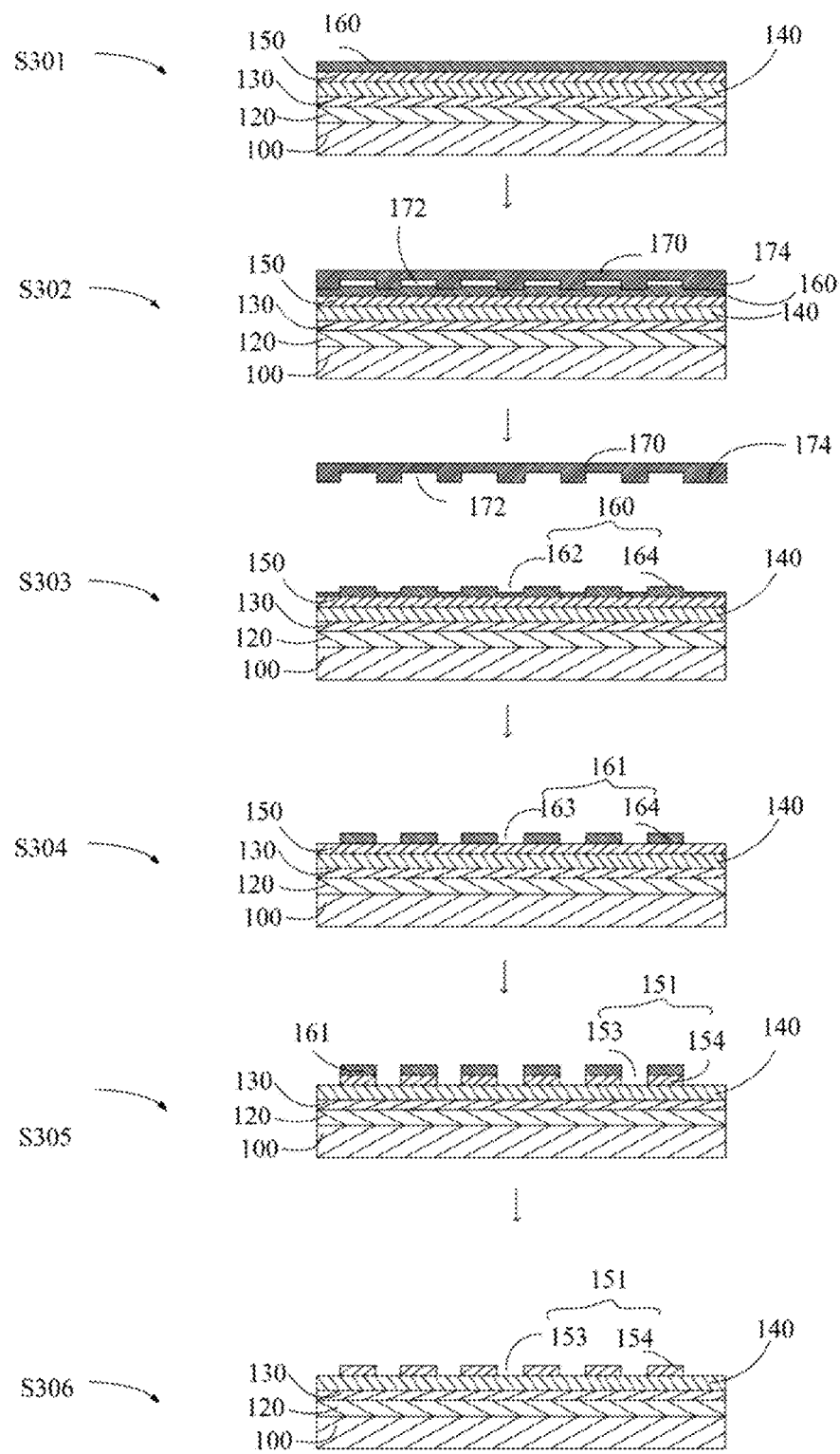
FIG. 7 is a flow chart of one embodiment of a method of making a first mask layer with patterns.

Referring to FIG. 7, the nanoimprinting method for making the first mask layer 151 on the second metal layer 140 comprises:

S301, providing a first mask layer preform 150 and a second mask layer preform 160 in that order on the second metal layer 140;

S302, providing a template 170 with nanoscale patterned surface, bonding the nanoscale patterned surface of the template 170 to the second mask layer preform 160 at room temperature, then pressing the template 170 and the second mask layer preform 160;

S303, removing the template 170 to transfer the nanoscale patterns of the template 170 to the surface of the second mask layer preform 160, wherein a fifth recessed portion 162 and a fifth convex portion 164 are formed on the surface of the second mask layer preform 160;

S304, removing a part of the second mask layer preform 160 to form a second mask layer 161 which defines a fifth opening 163, wherein the part of the second mask layer preform 160 corresponds to the fifth recessed portion 162, and a part of the first mask layer preform 150 corresponding to the fifth opening 163 is exposed;

S305, removing the part of the first mask layer preform 150 that is exposed;

S306, removing the second mask layer 161 to obtain a first mask layer 151.

In step S301, the material of the first mask layer preform 150 can be homemade photoresist or commercial photoresist, such as polymethylmethacrylate(PMMA), silicon on glass(SOG), ZEP520, hydrogen silsesquioxane(HSQ), SAL601. In one exemplary embodiment, the material of the first mask layer preform 150 is ZEP520.

The photoresist can be provided by spin coating or droplet coating. The method for making the first mask layer preform 150 comprises following steps: firstly, spin coating photoresist on the second metal layer 140, wherein the rotation speed can be in a range of 500 rpm to 6000 rpm, and the time can be in a range of 0.5 minutes to 1.5 minutes; secondly, baking the photoresist at an oven temperature of 140 degrees to 180 degrees for 3 minutes to 5 minutes. The first mask layer preform 150 is formed on the surface of the second metal layer 140. The thickness of the first mask layer preform 150 can be in a range of 160 nanometers to 380 nanometers. In one exemplary embodiment, the thickness of the first mask layer preform 150 is 260 nanometers.

The second mask layer preform 160 can be imprinted at room temperature, also should have good structural stability and high resolution. For example, the impression resolution of the second mask layer preform 160 can be less than 10 nanometers. The material of the second mask layer preform 160 can be HSQ, SOG, or other silicone oligomers. The thickness of the second mask layer preform 160 can be in a range of 80 nanometers to 280 nanometers. Furthermore, the thickness of the second mask layer preform 160 can be in a range of 100 nanometers to 160 nanometers. In one exemplary embodiment, the thickness of the second mask layer preform 160 is 121 nanometers. Since the second mask layer preform 160 can be mechanically embossed easily, the accuracy of nanoscale patterns formed on the first mask layer preform 150 is high. Thus the accuracy of etching the second metal layer 140 is high. In one exemplary embodiment, the material of the second mask layer preform 160 is HSQ. The state of HSQ is water-soluble vitreous with good mobility at room temperature, and become a cross-linked state after dehydration. The HSQ can flow spontaneously into channels of the template under pressure.

The method for making the second mask layer preform 160 comprises following steps: firstly, spin coating the resist HSQ on the first mask layer preform 150, wherein the rotation speed is in a range of 3000 rpm to 6500 rpm, and the spin-coating time is in a range of 0.6 minutes to 1.8 minutes, the spin coating of the HSQ is performed under high pressure; secondly, curing the resist HSQ to form a second mask layer preform 160.

In step S302, the template 170 can be a positive template or a negative template. In one exemplary embodiment, the template 170 is a negative template. The template 170 includes a plurality of spaced sixth recesses 172 and a plurality of sixth convex portions 174 between adjacent sixth recesses 172. The sixth recesses 172 can be stripe-shaped recesses or lattice-shaped recesses. In one exemplary embodiment, the sixth recesses 172 are stripe-shaped recesses, the sixth convex portions 174 are stripe-shaped convex portions, the sixth recesses 172 and the sixth convex portions 174 are arranged alternately. Furthermore, the sixth recesses 172 extend along the straight line to the edges of the template 170. Each sixth recess and sixth convex portion form an unit. The length of the unit can be in a range of 90 nanometers to 1000 nanometers. Furthermore, the length of the unit can be in a range of 121 nanometers to 650 nanometers. The width of the sixth recess 172 can be equal to the width of the sixth convex portions 174 or not. The width of the sixth recess 172 can be in a range of 40 nanometers to 450 nanometers. The width of the sixth convex portions 174 can be in a range of 50 nanometers to 450 nanometers. In one exemplary embodiment, the length of the unit is 200 nanometers, the width of the sixth recess 172 is 100 nanometers. The height of the sixth convex portions 174 can be in a range of 10 nanometers to 1000 nanometers. Furthermore, the height of the sixth convex portions 174 can be in a range of 20 nanometers to 800 nanometers. Furthermore, the height of the sixth convex portions 174 can be in a range of 30 nanometers to 700 nanometers. In one exemplary embodiment, the height of the sixth convex portions 174 is 200 nanometers.

The material of the template 170 can be hard materials such as nickel, silicon, or silicon dioxide. The material of the template 170 can also be flexible materials such as PET, PMMA, or PS. In one exemplary embodiment, the material of the template 170 is silicon dioxide.

The surface having nanoscale patterns of the template 170 is bonded to the second mask layer preform 160 at room temperature. When the template 170 is pressed, the degree of vacuum is in a range of $5 \times 10^{-4}$-$1.5 \times 10^{-2}$ bar and the applied pressure is in a range of 2 Psi to 100 Psi, and the time of applying pressure is in a range of 2 minutes to 30 minutes. In one exemplary embodiment, the degree of vacuum is $10^{-3}$ bar, the applied pressure is 25 Psi, the time of applying pressure is 5 minutes.

The sixth convex portions 174 of the template 170 are presses into the inside of the second mask layer preform 160 and the second mask layer preform 160 is deformed under the pressure to form a preform layer having nanoscale patterns. The part of the second mask layer preform 160 corresponding to the sixth convex portions 174 is compressed to form the fifth recesses 162. The HSQ flows into the sixth recess 172 of the template 170 under pressure, and the fifth convex portion 164 is formed on the second mask layer preform 160.

In step S303, a plurality of parallel and spaced fifth recesses 162 and fifth convex portions 164 are formed on the preform layer after removing the template 170. The size and shape of the fifth recesses 162 are the same as that of the sixth convex portions 174. The size and shape of the fifth convex portions 164 are the same as that of the sixth recesses 172. The depth of the fifth recesses 162 is in a range of 100 nanometers to 190 nanometers.

In step S304, the part of the second mask layer preform 160 corresponding to the fifth recesses 162 can be removed by plasma etching method. The etching gas can be selected according to the material of the second mask layer preform 160. In one exemplary embodiment, the part of the second mask layer preform 160 can be removed by fluorocarbon ($CF_4$) reactive plasma etching to form the second mask layer 161. The power of the $CF_4$ reactive plasma etching is in a range of 10 watts to 150 watts; the volumetric flow rate of the $CF_4$ plasma is in a range of 2 sccm to 100 sccm (standard-state cubic centimeter per minute); the pressure is in a range of 1 Pa to 15 Pa, the etching time is in a range of 2 seconds to 4 minutes. In one exemplary embodiment, the power of the etching system is 40 watts, the volumetric flow rate of the $CF_4$ plasma is 26 sccm, the pressure is 2 Pa, and the etching time is 10 seconds. The part of the second mask layer preform 160 corresponding to the fifth recesses 162 are removed by etching to form the fifth openings 163. The part of the second mask layer preform 160 corresponding to the fifth convex portions 164 is simultaneously etched and become thinner. The height of the fifth convex portions 164 is in a range of 90 nanometers to 180 nanometers.

In step S305, the part of the first mask layer preform 150 can be removed by oxygen gas plasma to form the first mask layer 151. The power of the oxygen gas plasma system is in a range of 10 watts to 250 watts, the volumetric flow rate of oxygen gas plasma is in a range of 2 sccm to 100 sccm, the air pressure is in a range of 0.5 Pa to 50 Pa, the etching time is in a range of 5 seconds to 5 minutes. In one exemplary embodiment, the power of the oxygen gas plasma system is 78 watts, the volumetric flow rate of oxygen gas plasma is 12 sccm, the air pressure is 26 Pa, the etching time is 30 seconds. After the part of the first mask layer preform 150 being removed, the first mask layer preform 150 defines a fourth opening 153 corresponding to the fifth opening 163. The second metal layer 140 corresponding to the fourth opening 153 is exposed. Since the HSQ is crosslinked under oxygen gas plasma, the fifth convex portions 164 can allow the first mask layer 151 to have a high resolution.

In step S306, the second mask layer 161 can be removed by solvent. Since the second mask layer 161 can be dissolved and the first mask layer 151 can not be dissolved by the solvent, when the second mask layer 161 is removed, the first mask layer is exposed and not removed. In one exemplary embodiment, the solvent is water. After the second mask layer 161 being removed, the body 154 of the first mask layer 151 is exposed, and the body 154 corresponds to the fifth convex portions 164.

In step S40, the structure obtained after the step S30 is placed in a reactive plasma system for etching, thus a plurality of parallel and spaced triangular prism structures 141 are obtained, the plurality of triangular prism structures 141 are arranged. The etching gas in the etching system is a mixed gas of a physical etching gas and a reactive etching gas. The physical etching gas can be argon gas, or helium, and the reactive etching gas can be oxygen gas, chlorine, boron trichloride, or tetrachloride carbon. The physical etching gas and the reactive etching gas can be selected according to the material of the second metal layer 140 and the first mask layer 151 so that the etching gas has a higher etching rate. For example, when the material of the second metal layer 140 is gold, platinum, or palladium, the physical etching gas is argon gas. When the material of the second metal layer 140 is copper, the physical etching gas is helium. When the material of the second metal layer 140 is aluminum, the physical etching gas is argon gas. In one exemplary embodiment, the physical etching gas is argon gas, and the reactive etching gas is oxygen gas.

The physical etching gas and the reactive etching gas are introduced into the etching system. On the one hand, the body 154 of the first mask layer 151 is progressively etched by the reactive etching gas; on the other hand, the exposed second metal layer 140 can also be etched by the physical etching gas. As the first mask layer 151 is progressively etched, the width of the fourth opening 153 gradually becomes greater. Since the exposed part of the second metal layer 140 corresponds to the fourth opening 153, the etching width of the exposed part gradually becomes greater from bottom to top. The first mask layer 151 can be removed or partially removed by the reactive etching gas. The exposed part of the second metal layer 140 can be removed or partially removed by the physical etching gas. The ratio between the horizontal etching rate and the vertical etching rate can be selected by adjusting the relationship of volumetric flow, pressure and power of argon gas and oxygen gas. The triangular prism structures 141 can be obtained by adjusting the ratio. The second metal layer 140 defines a plurality of parallel and spaced third openings 143 and comprises a plurality of triangular prism structures 141. The isolation layer 130 is exposed through the third openings 143.

The volume flow rate of the physical etching gas is in a range of 20 sccm to 300 sccm. The volume flow rate of the reactive etching gas is in a range of 2 sccm to 20 sccm. The pressure of the etching system is in a range of 16 Pa to 180 Pa, the power of the etching system is in a range of 11 watts to 420 watts, and the etching time is in a range of 5 seconds to 3 minutes. In one exemplary embodiment, the volumetric flow rate of argon gas is 48 sccm, the volumetric flow rate of oxygen gas is 5 sccm, the pressure of the etching system is 26 Pa, the power of the etching system is 70 watts, and the etching time is in a range of 15 seconds to 20 seconds.

In step S50, a plurality of parallel and spaced second rectangular structures 131 can be obtained by etching the isolation layer 130. In one exemplary embodiment, the material of the isolation layer 130 is chromium, the etching gas is a mixed gas of oxygen gas and chlorine gas. The power of the reactive plasma system can be in a range of 5 watts to 210 watts. Furthermore, the power of the reactive plasma system can be in a range of 10 watts to 88 watts. In one exemplary embodiment, the power of the reactive plasma system is 22 watts. The volume flow rate of oxygen gas can be in a range of 3 sccm to 35 sccm, the volume flow rate of chlorine gas can be in a range of 6 sccm to 200 sccm. In one exemplary embodiment, the volume flow rate of oxygen gas is 5 sccm, and the volume flow rate of chlorine gas is 26 sccm, the air pressure is in a range of 8 Pa to 150 Pa, the pressure of the system is 26 Pa. The etching time is in a range of 5 seconds to 1 minutes. In one exemplary embodiment, the etching time is 15 seconds.

The isolation layer 130 defines a plurality of parallel and spaced second openings 133 and comprises a plurality of second rectangular structures 131. The second openings 133 is stripe shaped. The second openings 133 correspond to the third openings 143, and the second rectangular structures 131 correspond to the triangular prism structures 141. The first metal layer 120 is exposed through the second openings 133.

In step S60, the etching the first metal layer 120 is performed in a reactive plasma system.

The physical etching gas and the reactive etching gas are introduced into the etching system. The physical etching gas is argon gas, and the reactive etching gas is a mixture of chlorine gas and oxygen gas. The physical etching gas and the reactive etching gas simultaneously etch the first metal layer 120.

A plurality of first openings 123 are obtained by etching a part of the first metal layer 120 corresponding to the second openings 133. In addition, some metal particles or powders can be produced and fall off from the first metal layer 120 during the etching process. If there is no reactive etching gas, the metal particles or powders will accumulate along the sidewalls of the first openings 123 to form a thick edge, and that will also result in a large surface roughness of the sidewalls of the first openings 123. A gradient of the etching rate of the first metal layer 120 along each direction tends to be stable. Since the metal particles or powders are deposited on the bottom surfaces of the first openings 123, the accumulation of the metal particles or powders on the bottom surfaces of the first openings 123 is equal to a reduction in the vertical etching rate and also equal to an increase in the horizontal etching rate. The excess metal particles or powders deposited on the sidewalls of the first openings 123 can be etched by the reactive etching gas and the physical etching gas. The first rectangular structures 121 have a regular structure and a small surface roughness.

The volume flow rate of chlorine gas can be in a range of 1 sccm to 240 sccm. Furthermore, the volume flow rate of chlorine gas can be in a range of 1 sccm to 100 sccm. In one exemplary embodiment, the volume flow rate of chlorine gas is 5 sccm. The volume flow rate of oxygen gas can be in a range of 1 sccm to 260 sccm. Furthermore, the volume flow rate of oxygen gas can be in a range of 1 sccm to 100 sccm. In one exemplary embodiment, the volume flow rate of oxygen gas is 10 sccm. The volume flow rate of argon gas can be in a range of 50 sccm to 500 sccm. In one exemplary embodiment, the volume flow rate of argon gas is 78 sccm. The pressure of the system can be in a range of 8 Pa to 110 Pa. In one exemplary embodiment, the pressure of the system is 16 Pa. The power of the system can be in a range of 20 watts to 300 watts. In one exemplary embodiment, the power of the system is 121 watts. The etching time can be in a range of 5 minutes to 50 minutes. Furthermore, the etching time can be in a range of 8 minutes to 13 minutes. In one exemplary embodiment, the etching time is 11 minutes.

The shape of the first openings 123 is regular rectangle after the step S60 being completed. The width of the first openings 123 is in a range of 10 nanometers to 350 nanometers. The width of the first openings 123 can be controlled by adjusting the etching time. The thickness of the first rectangular structures 121 can be controlled by adjusting the etching time. In one exemplary embodiment, the width of the first openings 123 is 150 nanometers.

Figure 8:
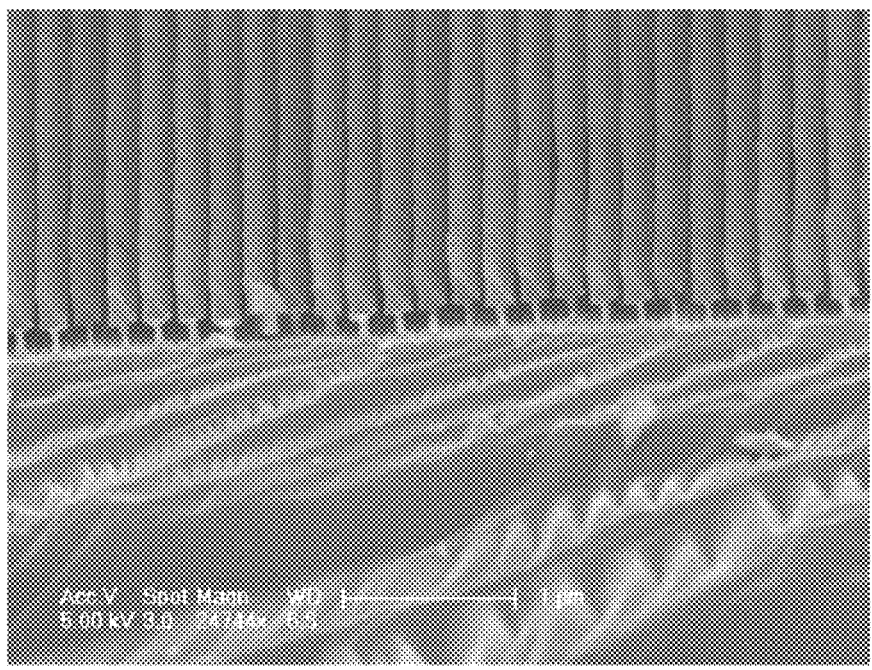
FIG. 8 is a low magnification Scanning Electron Microscope (SEM) image of the carrier.
Figure 9:
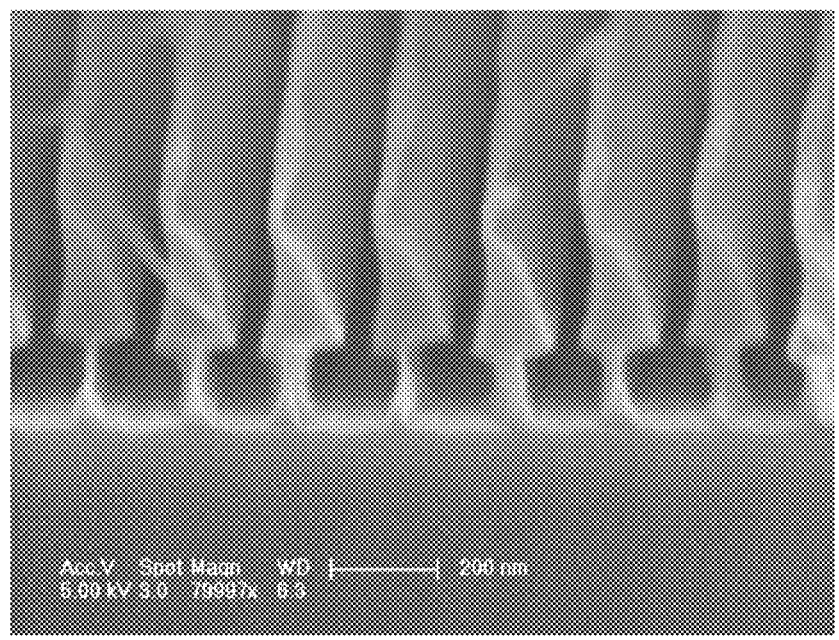
FIG. 9 is a high magnification Scanning Electron Microscope (SEM) image of the carrier.

In step S70, the residual photoresist remains in the structure obtained by step S60. The pine shaped metal nano-scaled grating 10 is obtained by removing the residual photoresist. The residual photoresist can be resolved by dissolving agent. The dissolving agent can be tetrahydrofuran (THF), acetone, butanone, cyclohexane, n-hexane, methanol, absolute ethanol, or non-toxic or low toxicity of environmentally friendly solvents. In one exemplary embodiment, the residual photoresist is removed by ultrasonic cleaning in acetone solution. FIG. 8 and FIG. 9 are SEM images of the pine shaped metal nano-scaled grating.

In step S2, the disposing single molecule samples includes the following sub-steps:
　　step 121, providing a single molecule sample solution;
　　step 122, immersing the carrier 10 into the single molecule sample solution; and
　　step 123, drawing the carrier 10 out of the single molecule sample solution.

In step 121, the molecular concentration of the single molecule sample solution can be in a range from about $10^{-7}$ mmol/L to about $10^{-12}$ mmol/L. In one embodiment, the molecular concentration of the single molecule sample solution is about $10^{-10}$ mmol/L.

In step 122, the carrier 10 is kept in the single molecule sample solution for a time from about 2 minutes to about 60 minutes so that the single molecule samples can be dispersed on the three-dimensional nanostructures 110 uniformly. In one embodiment, the carrier 10 is kept in the single molecule sample solution for about 10 minutes.

In step 123, the carrier 10 is rinsed in water or ethanol for about 5 times to about 15 times and dried after being drawn out of the single molecule sample solution.

In step 13, a Raman Spectroscopy system is used to detect the single molecule samples. In one embodiment, the Raman Spectroscopy system has an excitation source of He—Ne, an excitation wavelength of 633 nanometers, an excitation time of 10 seconds, a device power of 9.0 mW, and a working power of 9.0 mW×0.05×1.

Figure 10:
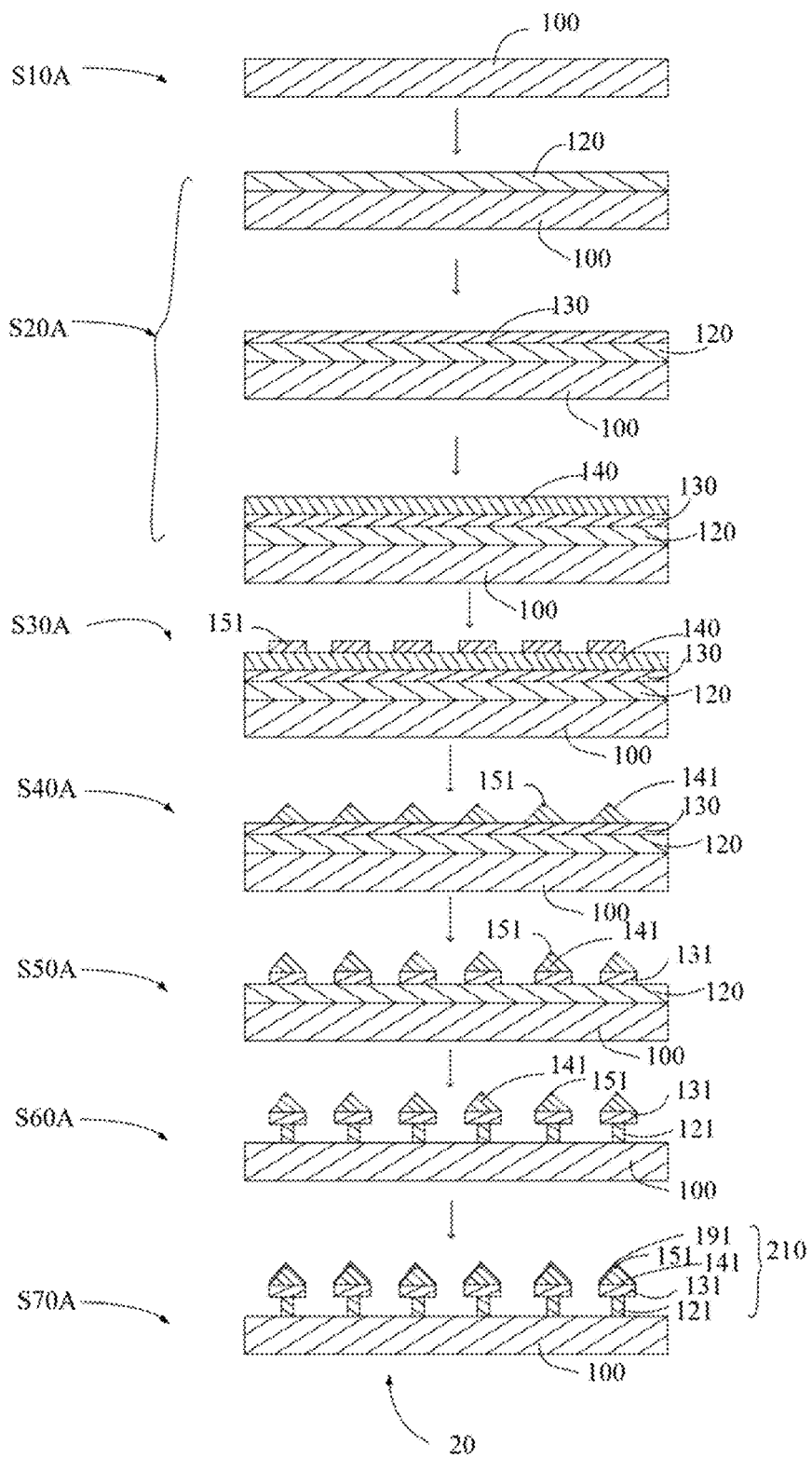
FIG. 10 is a flow chart of one embodiment of a method for making the carrier.

Referring to FIG. 10, an embodiment of a method of making the carrier 20 comprises:

S10A, providing a substrate 100;

S20A, forming a first metal layer 120 on the substrate 100, forming an isolation layer 130 on the first metal layer 120, and locating a second metal layer 140 on the isolation layer 130;

S30A, placing a first mask layer 151 on the second metal layer 140, wherein the first mask layer 151 covers partial surface of the second metal layer 140, and other surface is exposed;

S40A, etching the first mask layer 151 and the second metal layer 140 using the first mask layer 151 as a mask to obtain a plurality of parallel and spaced triangular prism structures 141;

S50A, etching the isolation layer 130 using the plurality of triangular prism structures 141 as a mask to obtain a plurality of parallel and spaced second rectangular structures 131;

S60A, etching the first metal layer 120 using the plurality of second rectangular structures 131 as a mask to obtain a plurality of parallel and spaced first rectangular structures 121; and S70, depositing a third metal layer 191 on the plurality of triangular prism structures 141 to obtain a three-dimensional nanostructures 210.

The method of making the carrier 20 is similar to the method of making the carrier 10 except that the third metal layer 191 is deposited on the triangular prism structures 141 without removing the first mask layer 151. The thickness of the third metal layer 191 is greater than 30 nanometers. In one exemplary embodiment, the thickness of the third metal layer 191 is 50 nanometers.

On the one hand, the method of depositing the third metal layer 191 on the triangular prism structures can adjust the charge distribution in the preparation process, which is beneficial to the processing. On the other hand, the mask layer does not need to be removed, so procedures of the method are simple. The pine shaped metal nano-scaled structure prepared by the above method can make the diffraction precision reach several hundred nanometers.

Figure 11:
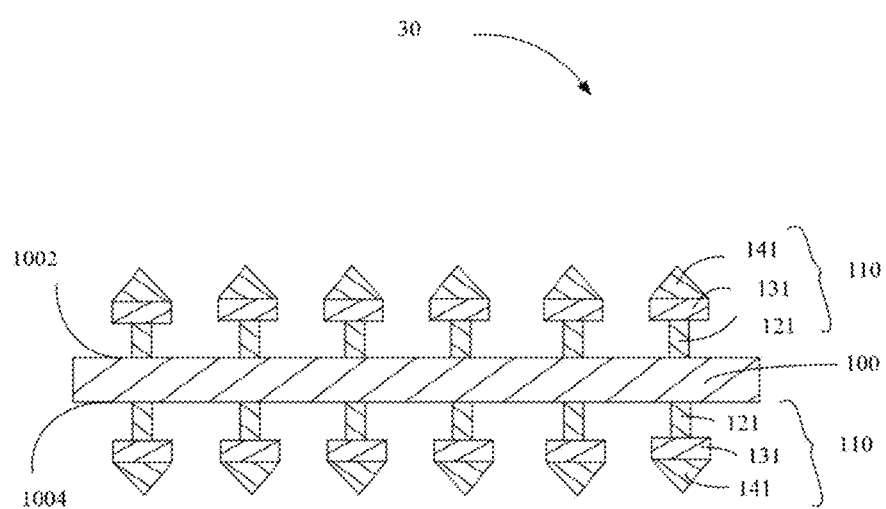
FIG. 11 is a structural schematic view of one embodiment of a carrier for single molecule detection.

Referring to FIG. 11, an embodiment of a carrier 30 comprises a substrate 100 and a plurality of three-dimensional nanostructures 110. The substrate 300 defines a first surface 1002 and a second surface 1004 corresponding to the first surface 1002. The plurality of three-dimensional nanostructures 110 are located on both the first surface 1002 and the second surface 1004. The three-dimensional nanostructures 110 comprises a first rectangular structure 121, a second rectangular structure 131, and a triangular prism structure 141. The first rectangular structure 121 is located on the substrate 100. The second rectangular structure 131 is located on the first rectangular structure 121. The triangular prism structure 141 is located on the second rectangular structure 131. The width of the bottom surface of the triangular prism structure 141 is equal to the width of the top surface of the second rectangular structure 131 and larger than the width of the top surface of the first rectangular structure 121.

The structure of the carrier 30 is similar to the carrier 10 except that the plurality of pine shape nanostructures 110 are located on both the first surface 1002 and the second surface 1004.

Figure 12:
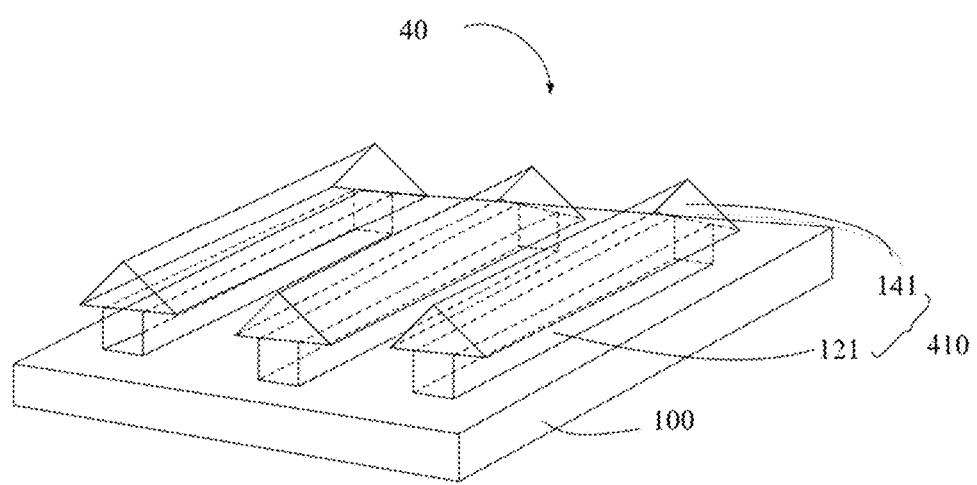
FIG. 12 is a structural schematic view of one embodiment of a carrier for single molecule detection.

Referring to FIG. 12, an embodiment of a carrier 40 comprises a substrate 100 and a plurality of three-dimensional nanostructures 410. The plurality of three-dimensional nanostructures 410 are located on at least one surface of the substrate 100. The three-dimensional nanostructure 410 comprises a rectangular structure 121 and a triangular prism structure 141. The rectangular structure 121 is located on the substrate 100. The triangular prism structure 141 is located on the rectangular structure 121. The width of the bottom surface of the triangular prism structure 141 is greater than the width of the top surface of the rectangular structure 121.

Figure 13:
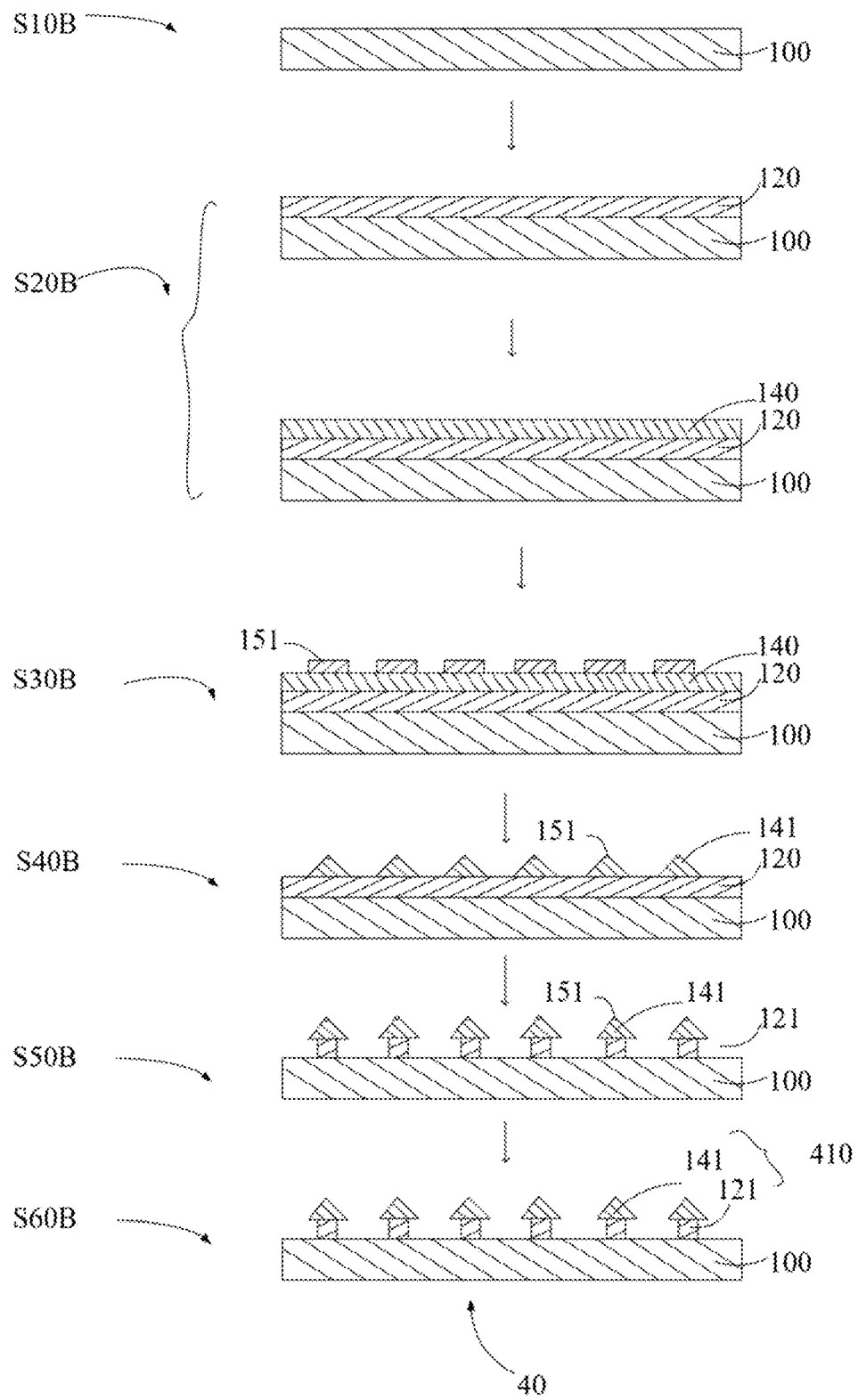
FIG. 13 is a flow chart of one embodiment of a method for making the carrier.

Referring to FIG. 13, an embodiment of a method of making the carrier 40 comprises:

S10B, providing a substrate 100;

S20B, forming a first metal layer 120 on the substrate 100, and locating a second metal layer 140 on the first metal layer 120;

S30B, placing a first mask layer 151 on the second metal layer 140, wherein the first mask layer 151 covers partial surface of the second metal layer 140, and other surface is exposed;

S40B, etching the second metal layer 140 to obtain a plurality of parallel and spaced triangular prism structures 141;

S50B, etching the first metal layer 120 to obtain a plurality of parallel and spaced rectangular structures 121; and S60B, removing the first mask layer 151 to obtain the carrier 40.

The structure of the carrier 40 is similar to the structure of the carrier 10 except that the pine shape structures consist of the rectangular structures 121 and the triangular prism structures 141. The material of the rectangular structures 121 and the triangular prism structures 141 is metal material. The material of the triangular prism structures 141 is different from the material of the rectangular structures 121.

The carrier of the disclosure includes a plurality of three-dimensional nanostructures. At the gap between two adjacent the plurality of three-dimensional nanostructures, a surface plasmon resonance (SPR) is produced so that the surface-enhanced Raman scattering (SERS) of the carrier will be outstandingly enhanced. The SERS is related to the spacing between the three-dimensional nanostructures. The smaller the spacing between the three-dimensional nanostructures, the larger the SERS.

The carrier of the disclosure has many advantages. The carrier consists of at least two metal layers, materials of the metal layers are metals with surface plasmons. Firstly, a surface plasmon resonance (SPR) is produced under the excitation of an incident photoelectric field. Secondly, the concavo-convex structure can enhance SERS, thus, the carrier can improve the resolution of single molecule detection.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size, and arrangement of the parts within the principles of the present disclosure up to, and including, the full extent established by the broad general meaning of the terms used in the claims.

Depending on the embodiment, certain of the steps of methods described may be removed, others may be added, and the sequence of steps may be altered. The description and the claims drawn to a method may comprise some indication in reference to certain steps. However, the indication used is only to be viewed for identification purposes and not as a suggestion as to an order for the steps.

What is claimed is:

1. A method of detecting single molecules, the method comprising:
   providing a carrier, wherein the carrier comprises a substrate, and a plurality of three-dimensional nanostructures are located on the substrate;
   disposing single molecule samples on the plurality of three-dimensional nanostructures; and
   detecting the single molecule samples with a detector;
   wherein each three-dimensional nanostructure comprises a first rectangular structure, a second rectangular structure, and a triangular prism structure; the first rectangular structure is located on the substrate, the second rectangular structure is located on the first rectangular structure, the triangular prism structure is located on the second rectangular structure, a first width of a bottom surface of the triangular prism structure is equal to a second width of a first top surface of the second rectangular structure and greater than a third width of a second top surface of the first rectangular structure, and the first rectangular structure comprises a first metal and the triangular prism structure comprises a second metal.

2. The method as claimed in claim 1, wherein the plurality of three-dimensional nanostructures are strip raised structures, and the plurality of three-dimensional nanostructures are arranged side by side and extend along a straight line, a fold line, or a curve line.

3. The method as claimed in claim 1, wherein the plurality of three-dimensional nanostructures are continuous or discontinuous along an extending direction.

4. The method as claimed in claim 1, wherein the bottom surface of the triangular prism structure is completely coincident with the first top surface of the second rectangular structure.

5. The method as claimed in claim 1, wherein two adjacent three-dimensional nanostructures are substantially parallel with each other, and a distance between the two adjacent three-dimensional nanostructures is in a range of 40 nanometers to 450 nanometers.

6. The method as claimed in claim 1, wherein the first metal is selected from the group consisting of gold, silver, copper, and aluminum; and the second metal is selected from the group consisting of gold, silver, copper, and aluminum.

7. The method as claimed in claim 1, wherein the second rectangular structure is selected from the group consisting of chromium, thallium pentoxide, titanium dioxide, silicon, and silica.

8. The method as claimed in claim 1, wherein a first thickness of the first rectangular structure is in a range of 20 nanometers to 500 nanometers, a second thickness of the second rectangular structure is in a range of 5 nanometers to 100 nanometers, and a third thickness of the triangular prism structure is in a range of 40 nanometers to 800 nanometers.

9. The method as claimed in claim 1, wherein the carrier further comprises a metal layer located on the triangular prism structure.

10. A method of detecting single molecules, the method comprising:
    providing a carrier, wherein the carrier comprises a substrate, and a plurality of three-dimensional nanostructures are located on the substrate;
    disposing single molecule samples on the plurality of three-dimensional nanostructures; and
    detecting the single molecule samples with a detector;
    wherein each three-dimensional nanostructure comprises a rectangular structure and a triangular prism structure, the rectangular structure is placed on the substrate, the triangular prism structure is located on the rectangular structure, the triangular prism structure comprises two second triangle surfaces and three rectangular surfaces, one of the three rectangular surfaces is defined as a bottom surface, a first width of the bottom surface of the triangular prism structure is greater than a second width of a top surface of the rectangular structure, the bottom surface of the triangular prism structure is in contact with the top surface of the rectangular structure, and the rectangular structure comprises a first metal and the triangular prism structure comprises a second metal, and the first metal is different from the second metal.

11. The method as claimed in claim 10, wherein the first metal is selected from the group consisting of gold, silver, copper, and aluminum; and the second metal is selected from the group consisting of gold, silver, copper, and aluminum.

12. The method as claimed in claim 10, wherein two adjacent three-dimensional nanostructures are substantially parallel with each other, and a distance between the two adjacent three-dimensional nanostructures is in a range of 40 nanometers to 450 nanometers.

13. The method as claimed in claim 10, wherein the plurality of three-dimensional nanostructures are strip raised structures, and the plurality of three-dimensional nanostructures are arranged side by side and extend along a straight line, a fold line, or a curve line.

14. The method as claimed in claim 10, wherein the carrier further comprises a metal layer located on the triangular prism structure.

* * * * *